United States Patent [19]
Riedel et al.

[11] Patent Number: 4,944,040
[45] Date of Patent: Jul. 31, 1990

[54] LIGHT OCCLUSIVE EYE PATCH

[75] Inventors: John E. Riedel, White Bear Lake; Frederick O. Olsen, Oakdale, both of Minn.

[73] Assignee: Minnesota Mining and Manufacturing Company, St. Paul, Minn.

[21] Appl. No.: 286,532

[22] Filed: Dec. 19, 1988

Related U.S. Application Data

[63] Continuation-in-part of Ser. No. 878,995, Jun. 26, 1986, Pat. No. 4,793,003.

[51] Int. Cl.$^5$ ............................................. A61F 9/04
[52] U.S. Cl. .......................................... 2/15; 128/858; 128/163
[58] Field of Search ................... 2/15, 12, 268, 174; 128/163, 858; 604/366, 371, 308, 386, 389; 106/499

[56] References Cited

U.S. PATENT DOCUMENTS

| | | | |
|---|---|---|---|
| Re. 24,906 | 12/1960 | Ulrich | 206/59 |
| 2,165,668 | 7/1939 | Vaccaro | 2/15 |
| 3,068,863 | 12/1962 | Bowman | 128/132 |
| 3,092,103 | 6/1963 | Mower | 128/132 |
| 3,121,021 | 2/1964 | Copeland | 117/122 |
| 3,285,245 | 11/1966 | Eldredge et al. | 128/156 |
| 3,844,865 | 10/1974 | Elton et al. | 156/229 |
| 3,870,593 | 3/1975 | Elton et al. | 161/159 |
| 3,908,645 | 9/1975 | Sandvig | 128/97 |
| 4,089,700 | 5/1978 | Brandt et al. | 106/499 X |
| 4,118,531 | 10/1978 | Hauser | 428/224 |
| 4,122,847 | 10/1978 | Craig | 128/132 |
| 4,167,503 | 9/1979 | Cipriani | 106/499 X |
| 4,539,256 | 9/1985 | Shipman | 428/315.5 |
| 4,598,004 | 7/1986 | Heinecke | 428/40 |
| 4,599,746 | 7/1986 | Stoner | 2/15 |
| 4,682,371 | 7/1987 | Heltman | 2/15 |
| 4,793,003 | 12/1988 | Riedel et al. | 2/15 |

FOREIGN PATENT DOCUMENTS 2605275  8/1976  Fed. Rep. of Germany .

OTHER PUBLICATIONS

Spanish Trade Literature of BDF Relating to "Elastopad" Product.

Primary Examiner—Peter Nerbun
Attorney, Agent, or Firm—Donald M. Sell; Walter N. Kirn; Carolyn A. Bates

[57] ABSTRACT

A light-occlusive self adherent eye patch is disclosed comprising an absorbent pad having a nonadherent lower surface, a backing having a lower face adhered to the upper surface of the pad and extending outward from the periphery thereof, a light-occlusive pressure sensitive adhesive coating on the lower face of the backing to adhere the patch to the eye socket, and a removable liner protecting the lower surface of the pad and the adhesive prior to use. The pressure sensitive adhesive blocks at least 95 percent of the light of a preselected wavelength impinging on the adhesive.

11 Claims, 1 Drawing Sheet

LIGHT OCCLUSIVE EYE PATCH

RELATED APPLICATIONS

This application is a continuation-in-part of application Ser. No. 878,995, filed June 26, 1986, now U.S. Pat. No. 4,793,003.

FIELD OF THE INVENTION

This invention relates to the field of light occlusive eye patches. More particularly, it relates to light-occlusive eye patches having a pressure sensitive adhesive on the peripheral portion of the patch to adhere the patch to the area of the body around the eye.

BACKGROUND ART

In the United States, strabismus (ambliopia) in children is most often corrected by surgical procedures. Non-surgical alternatives such as occlusive eye patches, fresnel eyeglass lenses, and the like are also available and are the first treatment of choice in Europe. The use of self-adhesive occlusive eye patches is quite common.

In occlusive therapy, an eye patch is applied daily over the nonaffected eye of the child. On average, the patch is worn for two hours each day, longer for older children, shorter for young children. There is some evidence in the literature to suggest that the efficacy of occlusive therapy is improved if the occlusive patch can be made so as to effectively prevent the passage of light to the nonaffected eye. The objective of occlusive therapy is to maintain the nonaffected eye (beneath the occlusive patch) immobile while the uncovered affected eye is free to move in response to visual stimuli. It is believed that small amounts of light passing through the occlusive patch to the nonaffected eye stimulate undesirable eye movement, thereby decreasing the efficacy of the treatment.

Criteria for an acceptable self-adhesive occlusive eye patch include the use of a gentle, hypoallergenic adhesive, softness and conformability to the eye socket, breathability, i.e., moisture vapor and air permeability to reduce the potential for skin damage, and cosmetic appeal. Furthermore, a light occlusive patch should effectively block the passage of ambient light without sacrificing any of the above requirements. Prior to the present invention, a self-adhesive occlusive eye patch having this combination of properties was not available.

A product known as Opticlude ® Orthoptic Eye Patch sold by 3M comprises an absorbent pad having nonadherent films on its upper and lower surfaces. A layer of skin-tone nonwoven medical tape, i.e., Micropore ® brand tape, overlies the adherent film on the upper surface of the pad and extends beyond the periphery of the pad in all directions to secure the patch to the eye socket. A removable liner protects the pad and adhesive layer prior to use.

Although Opticlude ® patches meet most of the criteria listed above, they effectively block only about 75 percent of the incoming ambient light. Several years ago attempts were made to modify the Opticlude ® product to make it light occlusive. A stiff, black, light-absorbing polyethylene film layer overcoated with a solid resin layer for skin toning was inserted between the nonwoven tape and the absorbent pad. In field testing, particularly in Germany, these patches reportedly caused skin irritation when worn and/or removed. The source of the irritation appeared to be the stiffness of the black film layer as well as the fact that the black film layer with its skin toned resin overcoat did not have good moisture vapor permeability.

Another product which has attempted to provide light occlusivity is Elastopad-lite occlusive plasters sold in Europe by Beiersdorf. This product is a laminate comprising an adsorbent pad, a layer of black nonwoven material and a layer of porous skin-tone polyvinyl chloride overlying the black nonwoven layer. A piece of skin-toned tape overlies the polyvinyl chloride layer and extends beyond the periphery of the other layers of the patch to adhere the patch to the eye socket. While the Elastopad product is moisture vapor permeable and appears to block virtually all of the ambient light, it is relatively thick, and not sufficiently soft and conformable to insure maximum comfort.

In U.S. Pat. No. 4,793,003, a self adherent eye patch is disclosed which is thin, soft, breathable, conformable and comfortable to wear, and also blocks virtually all incoming light. This combination of desirable properties is provided by fabricating the eye patch from a thin microporous polymeric film which is both capable of blocking at least 95 percent of light in a preselected wavelength and permeable to moisture vapor. The preferred film of this type is a porous polyethylene film made in accordance with U.S. Pat. No. 4,539,256 and rendered light occlusive by the addition of pigment. The eye patch also comprises an absorbent pad and a pressure sensitive adhesive for adhering the eye patch to the skin around the eye.

BRIEF SUMMARY OF THE INVENTION

It has now been discovered that a conformable, moisture vapor permeable eye patch such as the original 3M Opticlude product can be made light occlusive by incorporating pigments or other light-absorbing materials into the pressure sensitive adhesive layer. Such light occlusive adhesive coatings can be used in combination with a wide range of conformable backings such as nonwoven webs, which alone are incapable of providing the requisite light occlusivity.

According to the present invention, there is provided a self-adherent eye patch comprising: an absorbent pad shaped to fit over the eye having a nonadherent lower surface for contacting the eye and an opposing upper surface; a moisture vapor permeable backing having a lower face adhered to the upper surface of said pad and extending beyond the periphery of said pad, a pressure sensitive adhesive on the lower face of said backing for adhering the eye patch to the eye socket and which adhesive is capable of blocking at least 95 percent of light in a preselected wave length impinging thereon; and a removable protective liner covering the nonadherent lower surface of the pad and the exposed portion of the pressure sensitive adhesive prior to use. The eye patch preferably has a moisture vapor permeability of at least 600 grams per square meter per 24 hours throughout and also preferably has a conformability value less than 800 grams, and most preferably less than 600 grams, when tested according to the test methods set forth hereinbelow.

The preferred light occlusive pressure sensitive adhesive is an acrylate copolymer adhesive such as disclosed in U.S Pat. No. Re. 24,906 (Ulrich) which has been pigmented so as to provide at least 95 percent light occlusivity. Preferably, to obtain uniform occlusivity, the pigment is combined with a carrier which is compatible with the adhesive, such as a polyolefin resin, in a conventional "master batching" process prior to incorporation into the adhesive.

A further aspect of the invention relates to a method of treating an eye defect or traumatized eye which benefits from light occlusive therapy by covering the appropriate eye with the self-adherent eye patch described above.

The self adherent eye patch of the present invention provides an eye patch which is thin, conformable, breathable throughout its entire area, cosmetically appealing, and capable of blocking virtually all of the ambient light throughout its entire area.

DETAILED DESCRIPTION OF THE DRAWINGS

The invention is further illustrated by reference to the accompanying drawings wherein like reference numerals refer to like elements.

Figure 1:
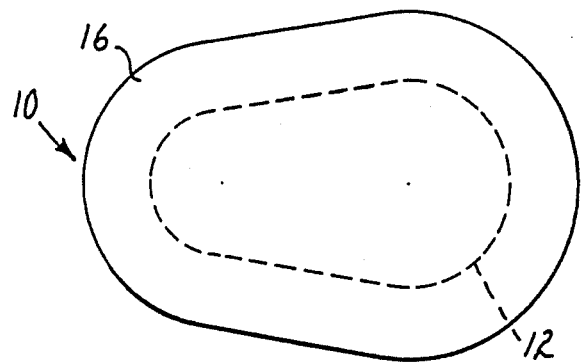
FIG. 1 is a top plan view of the eye patch of the invention.
Figure 2:
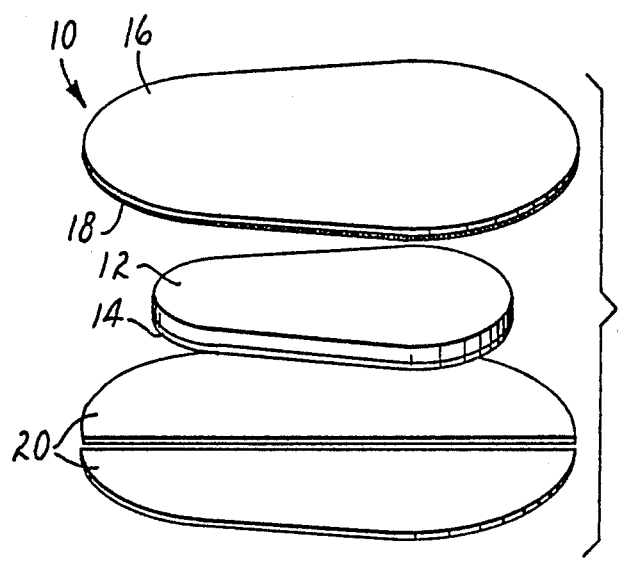
FIG. 2 is an exploded perspective view of the eye patch of FIG. 1.

Referring now to FIGS. 1 and 2, there is shown an eye patch 10 comprising an absorbent pad 12 shaped to fit over the eye having a nonadherent surface 14 on its underside for placing in contact with the eye. The upper surface of the absorbent pad 12 is adhered to a backing 16 by a layer of light-occlusive pressure sensitive adhesive 18. Adhesive 18 must be capable of blocking at least 95 percent of the ambient light. Backing 16 and adhesive 18 on the lower face thereof extend beyond the periphery of the absorbent pad 12 in all directions exposing enough adhesive 18 to securely adhere the eye patch to the eye socket. A removable protective liner 20 covers the nonadherent underside of absorbent pad 12 and the exposed pressure sensitive adhesive 18 prior to use.

The absorbent pad 12 provides cushioning and protection to the eye as well as fluid absorbency, and may comprise any of the accepted absorbent materials for surgical dressings, e.g., cotton, rayon, cellulosic batts, etc. The nonadherent surface 14 on the underside of the pad 12 prevents the pad from sticking to the eye and lint from the pad entering the eye. The nonadherent surface may be provided by any of the conventional methods known in the dressing art for preventing a dressing from sticking to a wound, and need not involve a separate layer of material. Preferably, the absorbent pad 12 and nonadherent surface 14 are constructed as described in U.S. Pat. No. 3,285,245 by heat bonding thermoplastic polymeric fibers or film such as polyethylene to the surface of a nonwoven web. The thermoplastic polymeric fibers or film melt and coalesce to form a discontinuous naturally porous film. The preferred absorbent pad 12 of this type comprises a needle-tacked rayon web similar to the pad used in the current 3M Opticlude ® product except the polyethylene nonadherent film covers only the lower surface of the pad which contacts the eye.

Pressure sensitive adhesive layer 18 provides light occlusivity to the eye patch. Light occlusivity can be obtained by dispersing suitable pigments into the adhesive prior to coating.

Pigments which can be used to render the adhesive light occlusive are preferably fine powders which can be dispersed in the adhesive and do not interfere with the coating of the adhesive onto the backing or transfer sheet. Dispersion of the pigment in the adhesive so as to obtain uniform light occlusivity throughout the adhesive layer is greatly facilitated by premixing the pigment with a suitable polymeric carrier which is compatible with the adhesive being used. Such pigment/carrier mixtures are well known in the pigment art and are made by conventional techniques known as master batching. For use with the preferred acrylate copolymer adhesives, a polyolefin, e.g., low density polyethylene carrier in a ratio of 50:50 pigment to carrier, has been found to be especially useful. The pigment is generally present in the range of 5 to 20 weight percent of the solids in the adhesive, preferably 10–15 percent by weight. Surprisingly, the addition of the pigment/carrier dispersion does not significantly affect the tackiness of the adhesive and the pigment maintains a stable dispersion in the adhesive.

In most cases, the pigmented adhesive will block transmission of light in all wave lengths, however, if desired for specific purposes, it may be possible to construct the adhesive layer so that light of a specific wave length, e.g., ultraviolet light, is blocked but some light in other wave lengths, e.g., visible light, is transmitted.

Pressure sensitive adhesive 18 may be any pressure sensitive adhesive commonly used on skin which is non-irritating and preferably has sufficient moisture vapor permeability to insure that the desired moisture permeability requirements of the overall eye patch are met. As indicated above, preferred adhesives are the acrylate copolymers described in U.S. Pat. No. Re. 24,906 such as a copolymer of isooctyl acrylate and acrylamide (96/4 or 97/3). Other suitable adhesive include polyvinyl ethers, polyurethanes and polyesters. Adhesive layer 18 is preferably between about 0.025 mm and 0.075 mm thick, which is provided by coating weights in the range of 25 g/m$^2$ to 75 g/m$^2$. If a continuous layer of an adhesive is not sufficiently moisture vapor permeable, it can be made microporous by conventional means to the extent that light occlusivity is not compromised. The preferred eye patches of the invention comprise nonwoven fabric backings, and the adhesive coated thereon is made microporous in the manner described in U.S. Pat. No. 3,121,021.

Backing 16 is also preferably moisture vapor permeable to the extent necessary to provide an overall moisture vapor permeability to the eye patch of at least 600 grams per square meter per 24 hours. Preferably, the backing is relatively thin, i.e., in the range of about 0.001 to 0.008 inch, soft and flexible so as to provide the eye patch with an overall conformability value of less than 800 grams in the method described below. Examples of suitable backings include a rayon nonwoven fabric such as that used in Micropore TM brand tape sold by Minnesota Mining and Manufacturing Company (3M) (described in U.S Pat. No. 3,121,021) a cellulose acetate taffeta fabric such as that used in Durapore TM brand tape, sold by 3M, a polyurethane film such as that used in Tegaderm TM brand transparent dressings sold by 3M (described in U.S. Pat. No. 4,598,004) and a polyurethane melt-blown nonwoven fabric such as that described in copending application Ser. No. 194,082, filed May 13, 1988. Other suitable backings include the microporous films described in U.S. Pat. No. 4,539,256 and 3,844,865. The backing is preferably pigmented with a skin-toned pigment to enhance the cosmetic appeal of the eye patch because the pigmented adhesive tends to be rather dark brown in color.

When applying eye patch 10 to a patient, the protective liner 20 is stripped from the eye patch, and the eye patch is applied over the eye with the absorbent pad 20 in contact with the eye and the adhesive portion of the eye patch adhered securely to the portion of the face surrounding the eye.

In addition to treating strabismus, the light occlusive eye patch of the invention may be used in the treatment of eye trauma wherein eye movement is painful or retards healing. Preventing light from entering the eye may help prevent undesirable eye movement. It is also possible to construct the eye patch to selectively occlude light of certain wave lengths while transmitting some visible light. A UV absorbing patch would be useful for protecting the eyes of small infants undergoing UV therapy or the eyes of people receiving UV radiation, as in commercial tanning studios.

Test Methods

The test methods used to measure moisture vapor permeability, air porosity, conformability and light occlusivity of the eye patches of the invention are set forth below.

Moisture Vapor Permeability

A modified Payne cup method is used. The method comprises the following steps:

(1) A 1⅜ inch (35 mm) diameter sample of materials to be tested containing no perforations is cut.

(2) The sample is centered between the adhesive surfaces of two foil adhesive rings, each having a one-inch (2.54 cm) diameter hole. The holes of each ring are carefully aligned. Finger pressure is used to form a foil/sample/foil assembly that is flat, wrinkle-free and has no void areas in the exposed sample.

(3) A 4-ounce glass jar is filled half full of distilled water. The jar is fitted with a screw on cap having a 1.5 inch diameter hole in the center thereof and with a 1.75 inch diameter rubber washer having a 1.12 inch diameter hole in its center.

(4) The rubber washer is placed on the lip of the jar and the foil/sample assembly is placed on the rubber washer. The lid is then screwed loosely on the jar.

(5) The assembly is placed in a chamber at 100° F. (38° C.) and 20 percent relative humidity for four hours.

(6) The cap is tightened inside the chamber so the sample material is level with the cap (no bulging) and the rubber washer is in proper seating position.

(7) The assembly is removed from the chamber and weighed immediately to the nearest 0.01 gram (initial weight $-W_1$).

(8) The assembly is returned to the chamber for at least 18 additional hours.

(9) The assembly is removed from the chamber and weighed immediately to the nearest 0.01 gram (final weight $-W_2$).

(10) The water vapor transmission in grams of water vapor transmitted per square meter of sample area in 24 hours is calculated according to the following formula:

$$MVT = \frac{(W_1 - W_2) \, 4.74 \times 10^4}{T \text{ (hours)}}$$

$W_1$ = initial weight (grams)
$W_2$ = final weight (grams)
$T$ = time (hours)

When a ½ inch sample is tested, the formula is changed to the following:

$$MVT = \frac{(W_1 - W_2) \, 1.9 \times 10^5}{T \text{ (hours)}}$$

(11) Three samples of each material should be run and the average taken.

Conformability

The conformability (i.e., softness, drape, etc.) of the eye patch is measured according to INDA Standard Test IST 90-75 (R77) Ring and Rod method, modified to accommodate a smaller sample Only the center pad portion of the eye patch (not the adhesive-coated tape portion extending outwardly from the pad portion) is tested. The test apparatus consists of two parts, which fit between the two jaws of an INSTRON® tensile tester and which are designed to draw apart. The upper part is in the form of an opensided cage, with a solid floor provided with a central ¾" hole. The lower part is a rod with a removable cap of 7/16" diameter. The rod moves in a vertical plane through the center of the hole in the cage. At the start of the test, a disc of the test sample, 1⅛" in diameter, is placed on the rod, pierced through its center and held in place by the cap. The rod is withdrawn through the hole and the force (in grams) is measured as the test sample is folded around the cap.

Light Occlusivity

Light occlusivity is measured using a Gardner Colorimeter Model XL-835 from Pacific Scientific Company, Bethesda, Md. using a method recommended by the manufacturer.

The eye patch of the present invention may be further illustrated by the following non-limiting examples.

EXAMPLE 1

A light-occlusive pressure sensitive adhesive was prepared from an isooctyl acrylate/acrylamide copolymer (97:3) made in accordance with U.S. Reissue No. 24,906 as a 25% solids solution in ethyl acetate/heptane (50/50). A pigment (C. B. Edwards #L-9322, pigment with low density polyethylene (55 parts pigment to 45 parts carrier) carrier resin mixed with the adhesive in the amounts shown below:

| INGREDIENT | TOTAL-PARTS | SOLIDS-PARTS |
|---|---|---|
| Adhesive | 1000 | 250 |
| Pigment | 54.1 | 54.1 (30 parts pigment) |
| TOTAL | 1054.1 | 304.1 (28.8% solids) |

After weighting into a suitable container the mixture was placed in a roller mill for 16 hours. Upon removal from the roller mill, the container was allowed to stand upright for 10 minutes prior to coating to allow entrapped air to escape.

The pigmented adhesive was coated using a hand-spread-knife over flat bed coater — with a 4 mil (0.1 mm) orifice to achieve the proper coating weight. Coating was applied to a one-sided silicone-coated liner (1-60-BKG-99AM from Daubert Coated Products, Dixon, IL) and dried one minute in air at room temperature and four minutes at 200° F. in an air circulating oven. The adhesive was applied at a coating weight of 30 g/m².

The adhesive coating was laminated to a backing comprising a 60 g/M² melt blown polyurethane fiber web prepared using thermoplastic elastomeric polyurethane polymer (PS 455-203, a polyesterurethane available from K. J. Quinn Co., Malden, MA) as the delivery matrix, and a fiber blend of 15 weight percent absorbent fiber (Lanseal ™ F, 2.5 denier, 51 mm staple length, available from Japan xlan Co., Ltd., Osaka, Japan), 70 weight percent wicking fiber (Avtex ™ Regular, a rayon fiber, 15 denier, 40 mm staple length, available from Avtex Corp., and 15 weight percent bulking fiber (Orlon ™ Type OT 670, 3 Denier, 38 mm staple length, available from DuPont Co.).

The web was prepared using a melt blowing process similar to that taught in U.S. Pat. No. 4,188,531 (Hauser) except that the melt-blowing die had circular smooth surfaced orifices (10/cm) with a 5:1 length-to-diameter ratio. The die temperature was maintained at 220° C., the primary air temperature and pressure were, respectively, 230° C. and about 150 kPa, (0.63 mm gap width), and the polymer throughput rate was 450 gm/hr/cm. The resulting web had a basis weight of 120 g/m² and contained 18.3 weight percent polyurethane microfiber having a fiber size of 5 to 10 microns and 81.7 weight percent staple fibers.

Lamination of the adhesive to the backing carried out using cold rolls at 1 Kg/lineal inch pressure on a Laminex laboratory laminator from Laminex, Inc., Matthews, NC. The transfer sheet was removed from the pressure sensitive adhesive and the backing was then laminated to an absorbent pad comprising a needled rayon web having a low density polyethylene film on one side (prepared according to U.S. Pat. No. 3,285,245) by placing the adhesive side of the pressure sensitive coated backing against the non-film side of the needled web and laminating the two webs on a laboratory laminator with no heat and 200 g/cm force on a 30-cm Laminex machine (Rexham Co., Matthews, North Carolina). A liner 2-80BKG-157 and 168A from Daubert Chemical Co. was applied to the adhesive side of the patch and covered the patch in two parts as illustrated in FIG. 2.

EXAMPLES 2-9

Additional eye patches were prepared as in Example 1, except for the differences noted in Table 1 below:

TABLE I

| Example | Differences from Example 1 |
| --- | --- |
| 2 | Backing had a basis weight of 80 g/M² |
| 3 | Backing had a basis weight of 120 g/M² |
| 4 | Backing was a rayon nonwoven fabric of the type used in Micropore ™ brand tape[1] |
| 5 | Backing was a polyurethane film of the type used in Tegaderm ™ Transparent Dressings |
| 6 | Backing was a cellulose acetate taffeta fabric[2] (80 g/m²) of the type used in Durapore ™ brandtape[1] Adhesive coating weight was 50 g/m² |
| 7 | Backing was same as Example 4 Adhesive had 9% pigment loading |
| 8 | Backing was same as Example 4 Adhesive had 5% pigment loading |
| 9 | Backing was same as Example 4 Adhesive had 0% pigment loading |

[1]3M Company, St. Paul, Minnesota
[2]Milliken Industries, Tacor, Georgia

The eye patches of Examples 1-9 were tested for light occlusivity, porosity, moisture vapor permeablility (MVT), and conformability in accordance with the test methods set forth hereinabove. The results are summarized in Table II.

TABLE II

| Ex. | % Light Occlusivity (backing & adhesive) | % Light Occlusivity (backing & adhesive & pad) | Porosity* (Seconds) | MVT g/m²/ 24 hrs | Conformability (grams) |
| --- | --- | --- | --- | --- | --- |
| 1 | 98.6 | 99.9 | 20 | 2200 | 122 |
| 2 | 99.9 | 99.9 | 30 | 1500 | 145 |
| 3 | 99.9 | 99.9 | 60 | 1600 | 167 |
| 4 | 99.3 | 99.9 | 5 | 3000 | 198 |
| 5 | 98.3 | 99.9 | 500+ (not porous) | 540 | 129 |
| 6 | 99.8 | 99.9 | 10 | 2400 | 236 |
| 7 | 95.4 | 99.2 | 5 | 2900 | 185 |
| 8 | 86.5 | 96.1 | 5 | 3000 | 178 |
| 9 | 29.0 | 74.0 | 5 | 3000 | 184 |

*Porosity was measured according to ASTM No. D-726-58, method A.

What is claimed is:

1. A self adherent eye patch comprising
an absorbent pad shaped to fit over the eye having a nonadherent lower surface for contacting the eye and an opposing upper surface;
a backing having a lower face adhered to said upper surface of said absorbent pad and extending outward from the periphery thereof;
pressure sensitive adhesive coating on the lower surface of said backing for adhering the eye patch to the eye socket; said adhesive being capable of blocking at least 95 percent of the light of a preselected wavelength impinging thereon;
a removable protective liner covering said nonadherent lower surface of said absorbent pad and the exposed portion of said pressure sensitive adhesive; and
said eye patch having a moisture vapor permeability of at least 600 grams per square meter per 24 hours throughout and a conformability value of less than 800 grams.

2. The eye patch according to claim 1 wherein said adhesive comprises one or more pigments which render said adhesive capable of blocking at least 95 percent of the light of a preselected wavelength impinging thereon.

3. The eye patch according to claim 2 wherein said pigment is mixed with a carrier which is compatible with said adhesive.

4. The eye patch according to claim 3 wherein said carrier is a polyolefin resin.

5. The eye patch according to claim 1 wherein said adhesive is an acrylate copolymer adhesive.

6. The eye patch according to claim 5 wherein said acrylate copolymer is a copolymer of isooctyl acrylate and acrylamide.

7. The eye patch according to claim 1 wherein said backing is a nonwoven web.

8. The eye patch according to claim 7 wherein said backing is a melt blown web of polyurethane fibers.

9. The eye patch according to claim 1 wherein said absorbent pad is a nonwoven web of rayon fibers and said nonadherent surface is formed from polyethylene film heat bonded to said rayon fibers.

10. A self adherent eye patch comprising:
an absorbent pad shaped to fit over the eye having a nonadherent lower surface for contacting the eye and an opposing upper surface;

a backing having a lower face adhered to said upper surface of said absorbent pad and extending outward from the periphery thereof;

pressure sensitive adhesive coating on the lower surface of said backing for adhering the eye patch to the eye socket; said adhesive being capable of blocking at least 95 percent of the light of a preselected wavelength impinging thereon; and a removable protective liner covering said nonadherent lower surface of said absorbent pad and the exposed portion of said pressure sensitive adhesive.

11. A method of treating an eye defect or trauma comprising the step of covering the appropriate eye with a self adherent eye patch which contains a layer of a pigmented pressure sensitive adhesive rendering said eye patch capable of blocking at least 95 percent of the light of a preselected wavelength impinging thereon.

* * * * *